(12) United States Patent
Clifton et al.

(10) Patent No.: US 6,682,550 B2
(45) Date of Patent: Jan. 27, 2004

(54) HEAT TRANSFER BLANKET FOR AND METHOD OF CONTROLLING A PATIENT'S TEMPERATURE

(75) Inventors: Guy L. Clifton, Houston, TX (US); Emmy R. Miller, Houston, TX (US)

(73) Assignee: The Board of Regents of the University of Texas, Austin, TX (US)

( * ) Notice: Subject to any disclaimer, the term of this patent is extended or adjusted under 35 U.S.C. 154(b) by 140 days.

(21) Appl. No.: 10/054,002

(22) Filed: Jan. 19, 2002

(65) Prior Publication Data

US 2002/0107558 A1 Aug. 8, 2002

Related U.S. Application Data

(63) Continuation-in-part of application No. 09/197,297, filed on Nov. 20, 1998, now Pat. No. 6,375,673, which is a continuation-in-part of application No. 09/065,156, filed on Apr. 23, 1998, now Pat. No. 6,113,626.

(51) Int. Cl.[7] ................................................. A61F 7/00
(52) U.S. Cl. ..................... 607/104; 607/108; 607/112
(58) Field of Search ........................ 607/104, 108, 607/112, 109

(56) References Cited

U.S. PATENT DOCUMENTS

| | | | | |
|---|---|---|---|---|
| 4,353,359 A | * | 10/1982 | Milbauer | 607/108 |
| 4,718,429 A | * | 1/1988 | Smidt | 607/104 |
| 5,230,335 A | * | 7/1993 | Johnson et al. | 607/104 |
| 5,263,336 A | * | 11/1993 | Kuramarohit | 607/104 |
| 5,383,919 A | * | 1/1995 | Kelly et al. | 607/104 |
| 5,411,541 A | * | 5/1995 | Bell et al. | 607/104 |
| 5,466,250 A | * | 11/1995 | Johnson et al. | 607/104 |
| 5,785,716 A | * | 7/1998 | Bayron et al. | 607/108 |
| 6,178,562 B1 | * | 1/2001 | Elkins | 607/108 |
| 6,228,106 B1 | * | 5/2001 | Simbruner et al. | 607/104 |
| 2003/0069621 A1 | * | 4/2003 | Kushnir | 607/104 |

* cited by examiner

Primary Examiner—Michael Peffley
(74) Attorney, Agent, or Firm—Kevin D. McCarthy; Roach, Brown, McCarthy & Gruber P.C.

(57) ABSTRACT

The present invention relates to heat transfer blankets which wrap the torso and/or legs leaving the arms, buttocks, perineum, knee, and/or head exposed and allow for the selective heating or cooling of various body parts at the same or different rates.

59 Claims, 15 Drawing Sheets

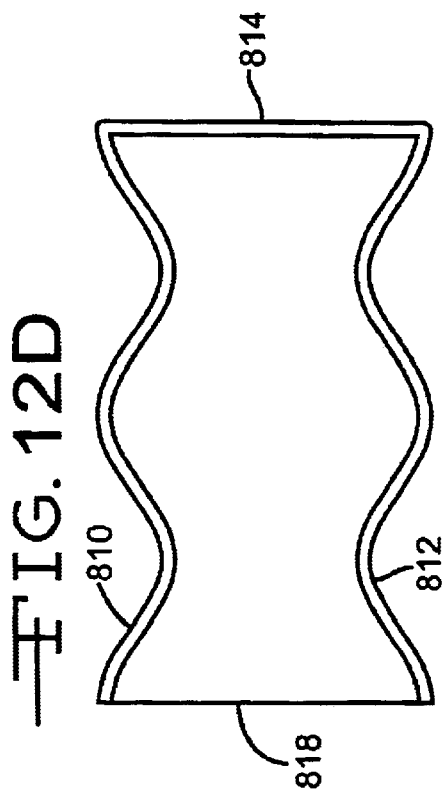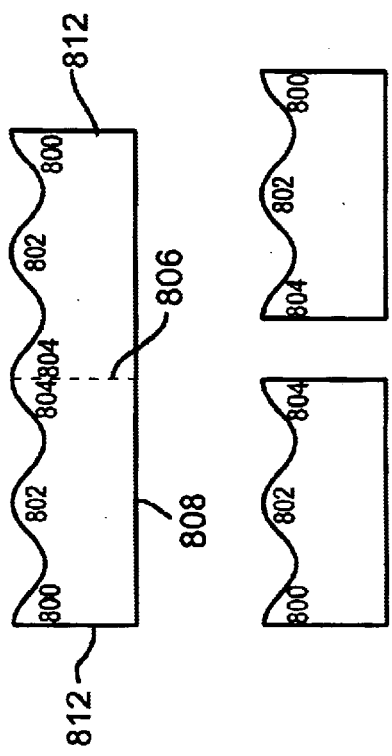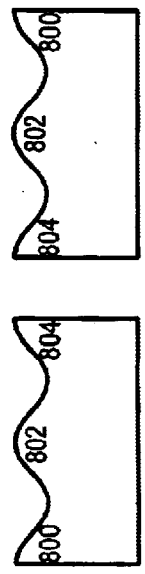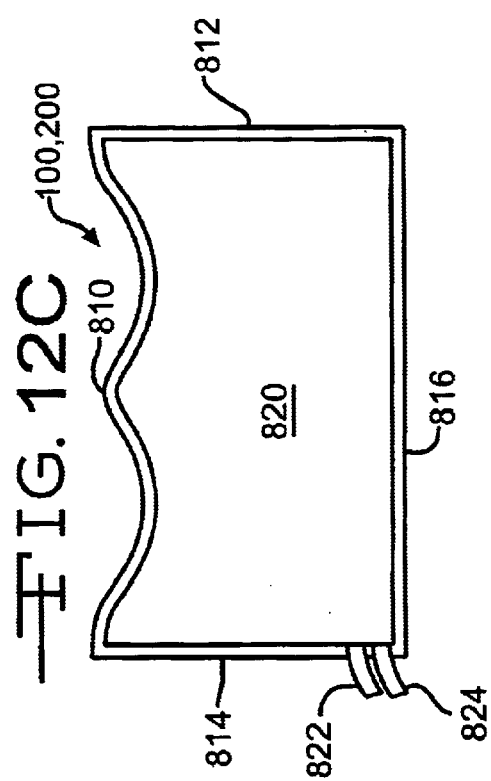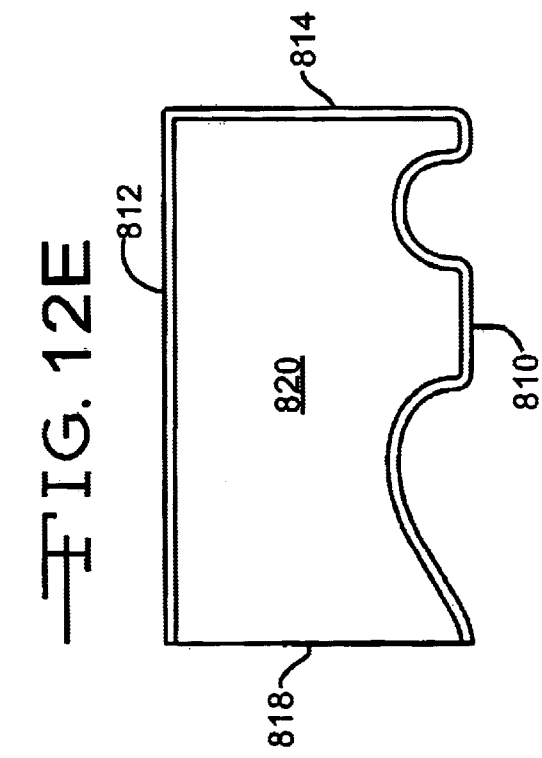

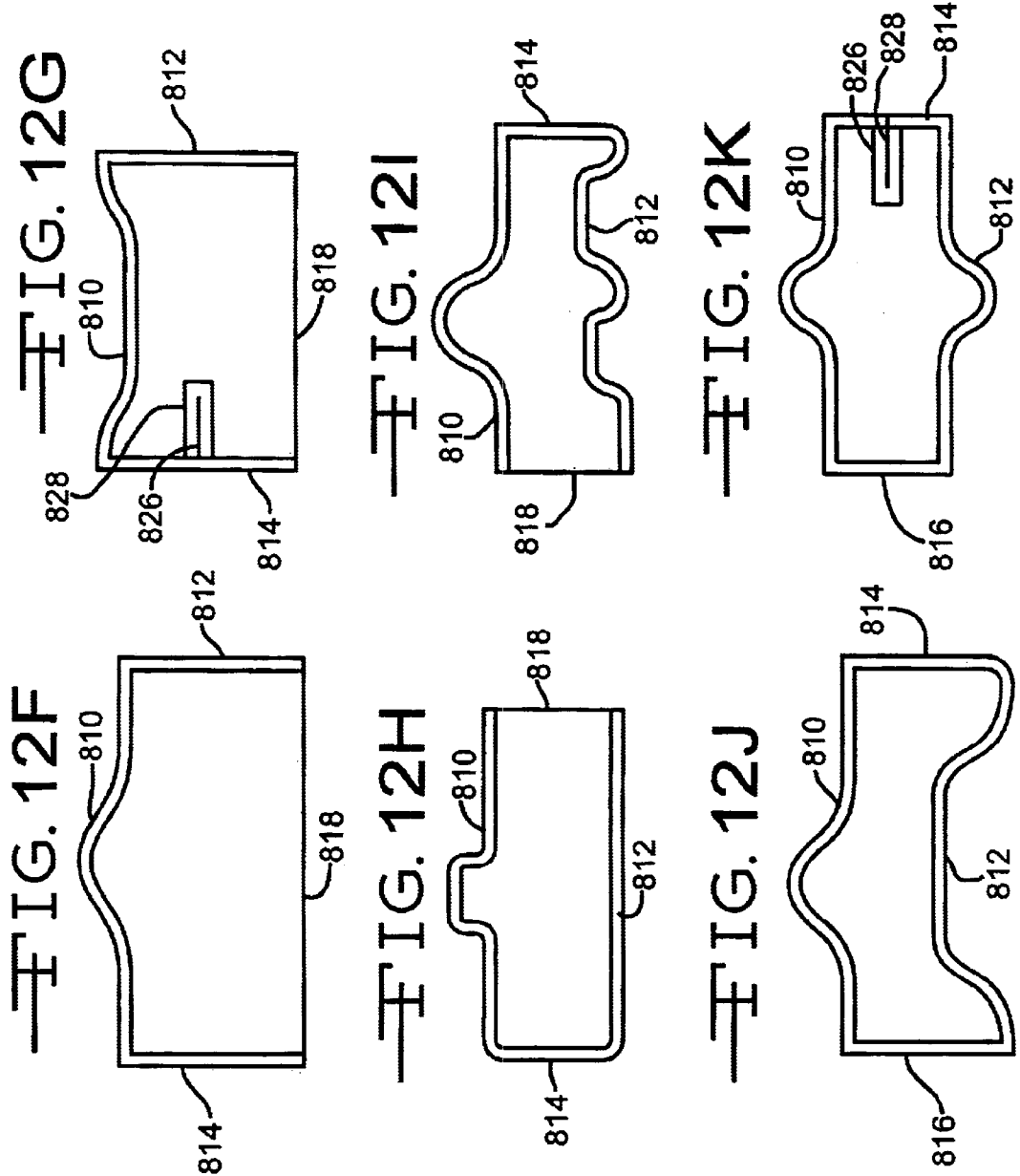

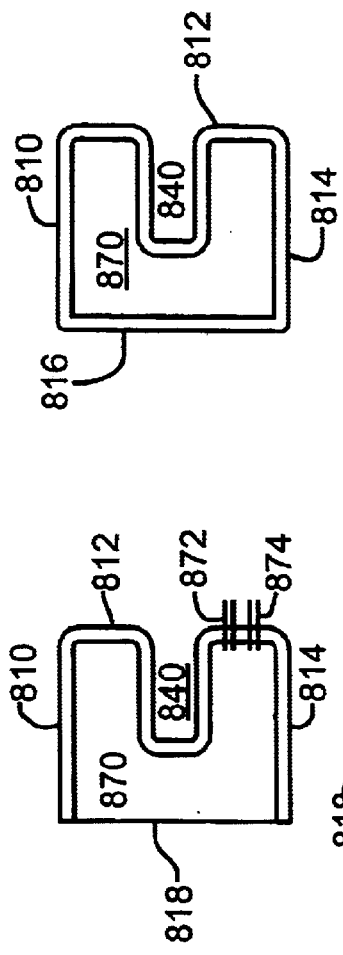
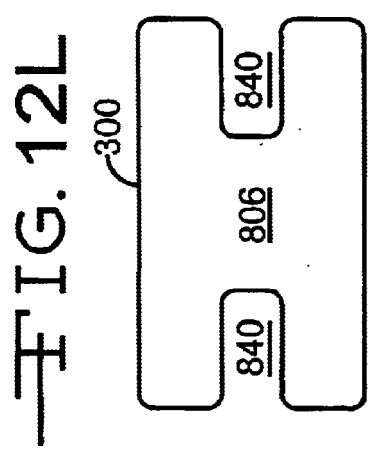
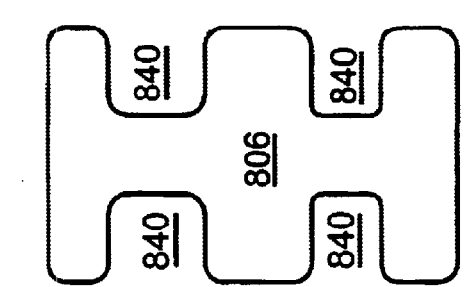

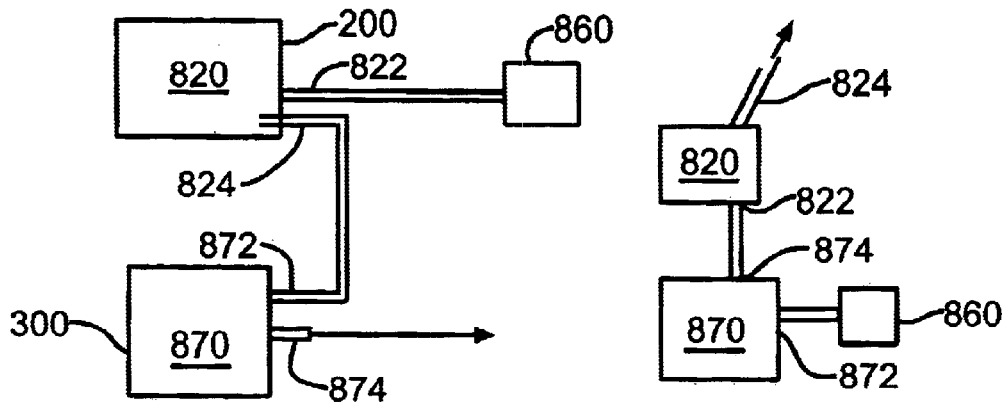
FIG. 13A
FIG. 13D
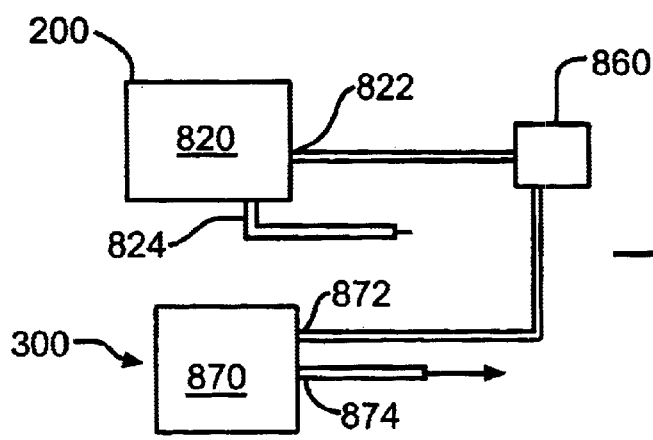
FIG. 13B
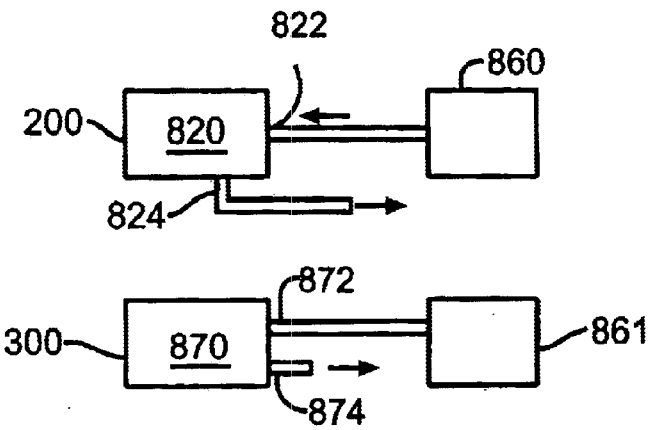
FIG. 13C

HEAT TRANSFER BLANKET FOR AND METHOD OF CONTROLLING A PATIENT'S TEMPERATURE

RELATED APPLICATION DATA

This application is a continuation-in-part of U.S. application Ser. No. 09/197,297, filed Nov. 20, 1998 (now U.S. Pat. No. 6,375,673), which is a continuation-in-part of U.S. application Ser. No. 09/065,156 filed Apr. 23, 1998 now U.S. Pat. No. 6,113,626.

BACKGROUND OF THE INVENTION

1. Field of the Invention

The present invention relates to a heat transfer system for and method of controlling a patient's temperature.

2. Description of the Related Art

Man is an animal with a normal functioning body temperature of about 37° C. Therefore, comfortable human survival requires a body's core temperature of about 37° C., +/− perhaps 1°. See, "Hypothermia—physiology, Signs, Symptoms and Treatment Considerations", Search and Rescue Society of British Columbia, compiled by Michael McEwan, 1995. The McEwan article further notes that a body can self compensate for small upward or downward variations in temperature through the actuation of a built-in thermal regulatory system, controlled by temperature sensors in the skin.

For example, the response to an upward variation in body temperature is the initiation of perspiration, which moves moisture from body tissues to the body surface, where evaporation causes cooling. Likewise, the response to a downward variation in body temperature is shivering, which is the body's involuntary contraction and expansion of muscle tissue on a large scale in an attempt to generate heat.

Stiff and Sixta, "Hypothermia Care and Prevention", 1997, generally define hypothermia as occurring when the body's core temperature drops below its normal 37° C. In contrast, the McEwan article defines impending hypothermia as occurring when the core temperature decreases to 36° C.

In the early stages mild hypothermia causes vigorous shivering which is usually accompanied by an increase in pulse and breathing rates. Cold, white hands and feet (as the blood vessels in the skin constrict) are the first signs of blood being shunted away from the body's extremities.

The McEwan article describes mild hypothermia as occurring when the core temperature is dropped to the range of 34–35° C. At this point, uncontrolled, intense shivering begins, although the victim is still alert and able to help itself, however, movements become less coordinated and the coldness creates some pain. Hypothermia occurs when the core temperature is in the range of 31 to 33° C. At this point shivering slows or stops, muscles begin to stiffen and mental confusion and apathy sets in. Speech becomes slow, vague and slurred with breathing becoming slower and shallower.

The McEwan article defines severe hypothermia as occurring when the body's core temperature is below 31° C.; Stiff and Sixta define severe hypothermia as resulting when the body temperature drops below 33° C. Shunting of the blood continues, manifesting as bluish lips and finger tips from poor oxygenation of the tissues near the body surface. Decreased circulation results due to a build-up of acid metabolites (waste products) in the muscles of the extremities until shivering stops and is replaced by muscular rigidity. The pulse and respirations slow as the body core cools to about 30° C. The heart may stop at temperatures of about 28° C. or less.

Hypothermia can occur during any outdoor excursion, especially in wilderness situations where weather conditions may deteriorate unexpectedly or where travelers become lost, get injured or exhaust food supplies prematurely. Additionally, outdoor activities involving water present the added possibility of emersion with the body cooling up to 25 times faster in water than in air.

Mild hypothermia is also a common occurrence during major surgery on the body. The usual causes of such perioperative hypothermia or anesthetic-induced impairment of thermal regulation include exposure to cold, altered distribution of body heat, and surgical exposure of the body cavity to a room temperature environment. The latter cause is particularly a problem in patients anesthetized for over two hours when there are large incisions exposing the body's interior to room temperature. Routine measures to reduce heat loss during operation include covering the skin, warming intravenous fluid and transfused blood, and increasing ambient temperature. In most operations, with the exception of those on the brain, prevention of hypothermia is a mainstay of anesthetic management because hypothermia during surgery can adversely affect the outcome. See "Colorectal Surgery Comes in From the Cold", The New England Journal of Medicine, Vol. 334, No. 19, Mortensen et al., May 19, 1996.

As discussed above, hypothermia may be encountered as a result of an accident or may be inadvertently acquired during major surgery. In an odd twist, hypothermia may be induced by a physician in the treatment of various conditions to protect the brain or heart. For example, U.S. Pat. No. 5,486,204, issued Jan. 23, 1996 to Clifton discloses a method of treating a non-penetrating head wound with hypothermia. Such a treatment protocol includes specific defined times, temperatures, rates of change of temperature and the timing of the introduction of medications, and controlled rewarming. Additionally, hypothermia is frequently induced during surgery for intra-cranial aneurysms.

The McEwan article notes that treatment of cold injuries has long been controversial. It is also clear that it is not enough merely to reheat a victim suffering from hypothermia, but that controlled heating must be applied. For example, Baron Larrey, Napoleon's Chief Surgeon observed that those soldiers, suffering from hypothermia, who were placed closest to the campfire during Napoleon's retreat from Russia died. These soldiers probably rewarmed too rapidly. It is generally accepted that treating hypothermia requires an emphasis on preventing further heat loss, rewarming as soon as it is safely possible at a successful rate (slowly) and rewarming the body core before the extremities in an attempt to avoid inducing lethal side effects during rewarming. This treatment goal is important since hypothermia itself may not be fatal above 25° C. core temperature. Fatalities at 25° C. or greater normally occur during rewarming.

The McEwan article notices that hypothermia causes several reactions within the body as the body tries to protect itself and retain its heat. One of the most important body reactions is vaso constriction, which halts blood flow to the extremities in order to conserve heat in the critical core area of the body. Shivering also generates peripheral vaso constriction, which minimizes the severity of vascular collapse during rewarming. Induction of vasodilation in hypothermia patients may precipitate rewarming shock and metabolic acidosis. This may occur where the periphery (legs and arms) are warmed before the core (heart and lungs) are warmed. Furthermore, the rapid shunting of cold blood from the extremities to the core, as a result of vasodilation, may cause the core temperature to drop. Prevention of vasodilation is a reason why it is imperative that the hypothermia victim's extremities not be rewarmed before the core. If vasodilation occurs, cold blood returning to the heart may be enough to put the patient into ventricular fibrillation. Again see, the McEwan article.

The McEwan article notes treatment for the different levels of hypothermia. According to McEwan, treatment for mild hypothermia includes keeping the head and neck covered. Stiff and Sixta note that treatment for mild hypothermia generally includes the application of hot packs, water bottles, or warm campfire rocks wrapped in towels to the groin, head, neck and sides of the chest. McEwan's treatment for moderate hypothermia includes keeping the head and neck covered, with mild heat applied to the head, neck, chest, armpits and groin of the hypothermia patient. For severe hypothermia, McEwan notes that treatment includes application of heat by skin to skin contact in the areas of the chest and neck with exhaled warm air or steam introduced near the patient's nose and mouth. Stiff and Sixta note that treatment for severe hypothermia will include application of hot packs to the neck, armpits, sides of chest and groin of the hypothermia victim, with the head kept covered.

Air warmed and cooled devices to maintain normothermia during surgery are available and in wide use. However, as many as 10% of patients are hypothermic during surgery despite use of these devices. They do not contact an adequate amount of body surface to either maintain normothermia during surgery for parts of the body other than the brain, or to safely induce hypothermia during brain surgery or after a head injury. The current lack of devices to effectively control a patient's temperature may result in poor clinical outcomes.

Prior to discussion of the details of the present invention, reference will first be made to a commonly used prior art blanket. Referring first to FIG. 1, there is shown an illustration of a patient 10 shown positioned on a prior art blanket B. The configuration of a prior art blanket shown generally in FIG. 1 is currently the only configuration commercially available to provide whole body surface cooling. A heat transfer fluid is circulated into and out of blanket B utilizing tubing 11 and 12 respectively. Notice how blanket B generally makes contact with only a limited portion of the skin surface of patient 10, generally the back or front body portion upon which patient 10 is resting. In the supine position, prior art blanket B does not contact the contour of the body. When blanket B contacts the posterior surface of patient 10, it only contacts the scapulae, the buttocks, and the posterior surface of the lower legs. If anterior, prior art blanket B contacts the area of the pectoralis muscles or breasts, the anterior aspect of the abdomen, and the anterior aspect of the upper leg and knee. In addition, in the operating room where a patient is on his side, prior art blanket B would only contact the side of the patient. Furthermore, due to its rectangular shape, prior art blanket B cannot wrap the legs or the trunk, thus leaving the majority of the body surface uncontacted by the blanket. In any of the above situations, the heat transfer area could be improved.

In 1992, one of the inventors utilized a modified non-commercial embodiment of a RotoRest bed (Kinetic Concepts, Inc.) in an hypothermia study. This bed had been equipped with cooling panels for wrapping the abdomen and chest. This bed does not have the capability of warming and cooling different body surfaces at the same time, the cooling apparatus cannot be used independently of the bed, and the bed cannot be used in the operating room or post operative room because of limitations imposed on patient care by the RotoRest bed.

Applicant is unaware of any prior art that discloses or suggests an apparatus for selective rewarming of a hypothermia patient to rewarm various body parts at different rates and at different temperatures to minimize the occurrence of vasodilation. Additionally, such references fail to disclose a suit which wraps the torso and legs leaving the arms, buttocks, perineum and head exposed.

For example, in the situation of a patient suffering from hypothermia or in whom hypothermia has been deliberately induced, exposure of the arms is necessary as they are the primary site for insertion of necessary intravenous lines. Exposure of the head is necessary to maintain control of the airway. The ability to gain ready access to the chest, back and abdomen (the core) is necessary should cardiopulmonary resuscitation be needed, to auscultate heart and breath sounds, to auscultate abdominal sounds or to provide exposure for surgeries of the chest, back or abdomen. Exposure of the legs is necessary for hygiene or for surgery of the legs. The perineum is always exposed in order to provide access to the urinary tract and also because of the significant hygiene issues associated with these sites where body wastes are eliminated. Firm contact of the blanket to the torso and legs, however, is necessary to control temperatures whether inducing hypothermia, maintaining hypothermia or rewarming. In a medical setting, however, ready access to the torso and legs and exposure of head, arms and perineum is required. None of the devices of the prior art meets these needs.

Thus, there is still a need in the art for apparatus for selective heating and cooling of various body parts of a human suffering from hypothermia so that various body parts can be heated and cooled at different rates and at different temperatures.

There is still another need in the art for an apparatus for heating and cooling of a patient in which the maximal body surface is in contact with the cooling/heating surface, which will also provide for easy access to the patient's body for either surgery or routine patient care, while the patient is being heated and/or cooled.

These and other needs in the art will become apparent to those of skill in the art upon review of this specification, including its drawing and claims.

SUMMARY OF THE INVENTION

The present invention relates to heat transfer blankets which wrap the torso and/or legs leaving the arms, buttocks, perineum, knee, and/or head exposed and allow for the selective heating or cooling of various body parts at the same or different rates.

BRIEF DESCRIPTION OF THE DRAWINGS

FIGS. 12a–r are alternative embodiments of the present invention and how to make the same.

FIGS. 13a–d illustrate block schematics of how the present invention operates.

DETAILED DESCRIPTION OF THE INVENTION

Figure 1:
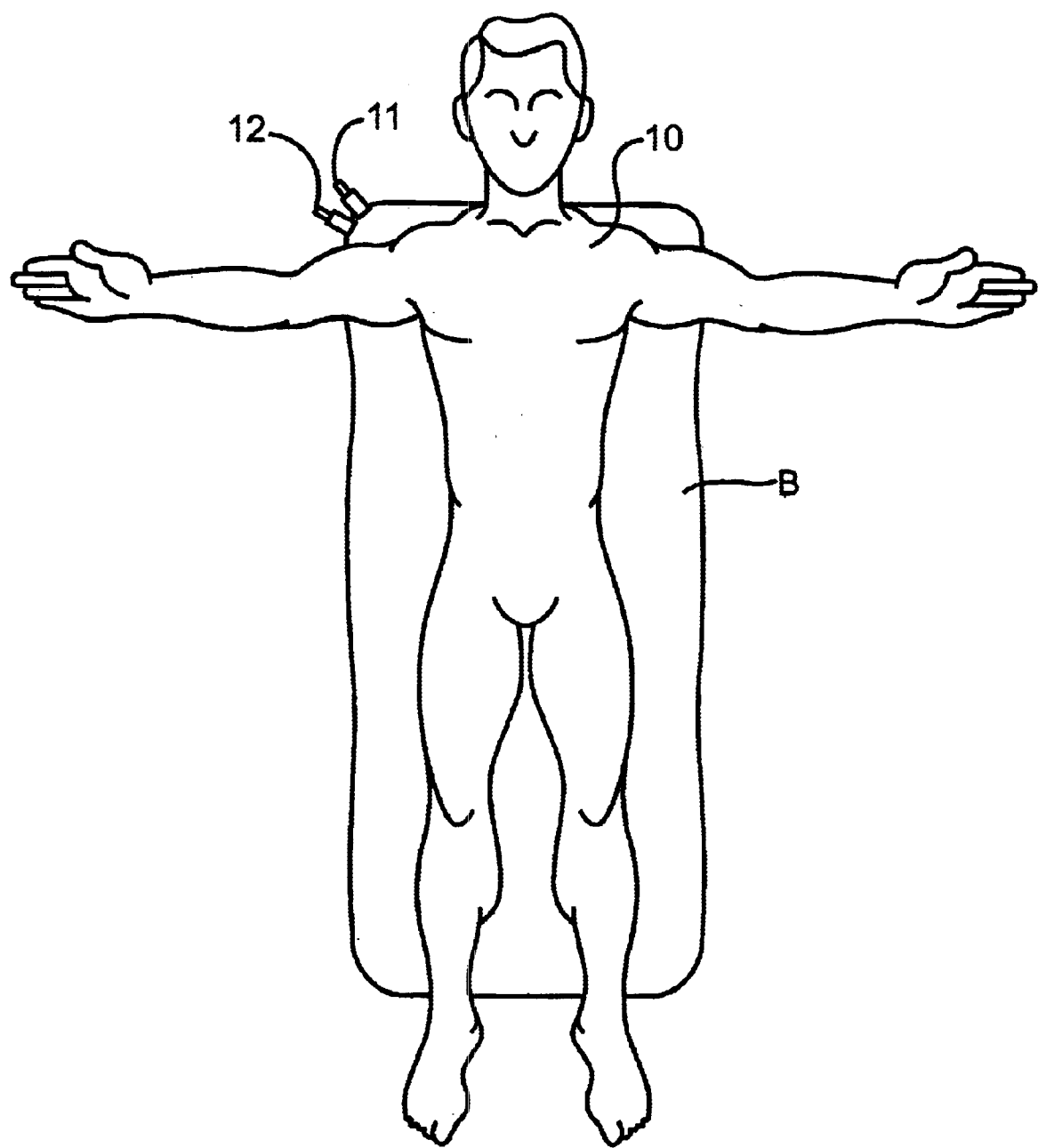
FIG. 1 is an illustration of a patient 10 shown positioned on a prior art blanket B.
Figure 2:
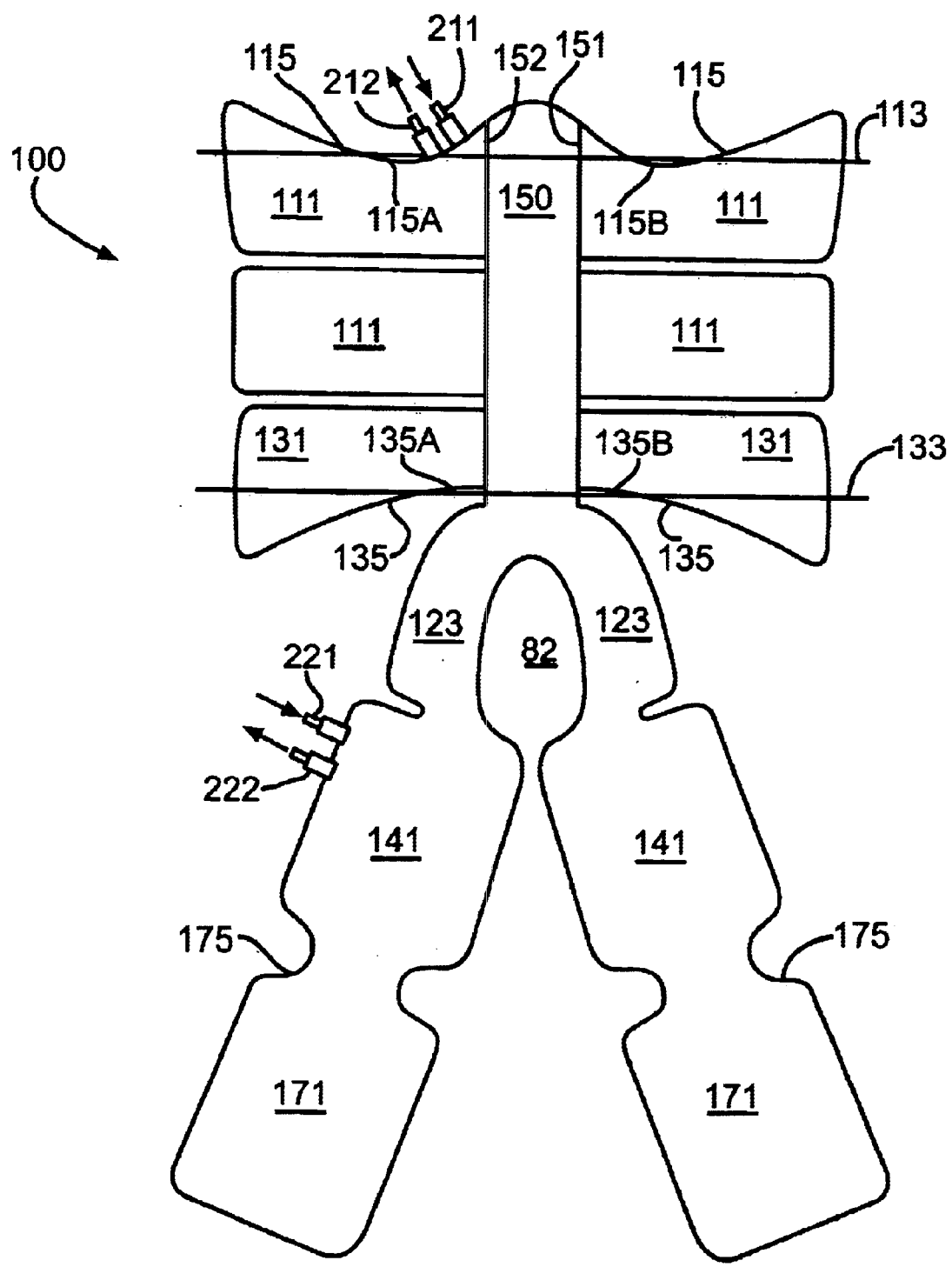
FIG. 2 is an illustration of one embodiment of a heating and cooling blanket 100 of the present invention with a main panel 150, chest panels 111, an abdomen panel 131, an upper leg panel 141, a lower leg panel 171, a cutout portion 175 between panels 141 and 171, projections 115 extending above an axillary line 113 of the patient 10 and projections 135 extending below an iliac line 133 of the patient 10.

The present invention will now be described by reference to FIGS. 2–12. Referring first to FIG. 2 there is shown one embodiment of a heating and cooling blanket 100 of the present invention, a main panel 150, an upper leg panel 141 and a lower leg panel 171 with a connecting area 123. The heating and cooling blanket 100 provides for the wrapping of the chest, abdomen, and upper and lower legs using various panels 111, 131, 141 and 171, respectively. These various panels may be opened for access during surgery, medical procedures or hygiene.

Figure 8:
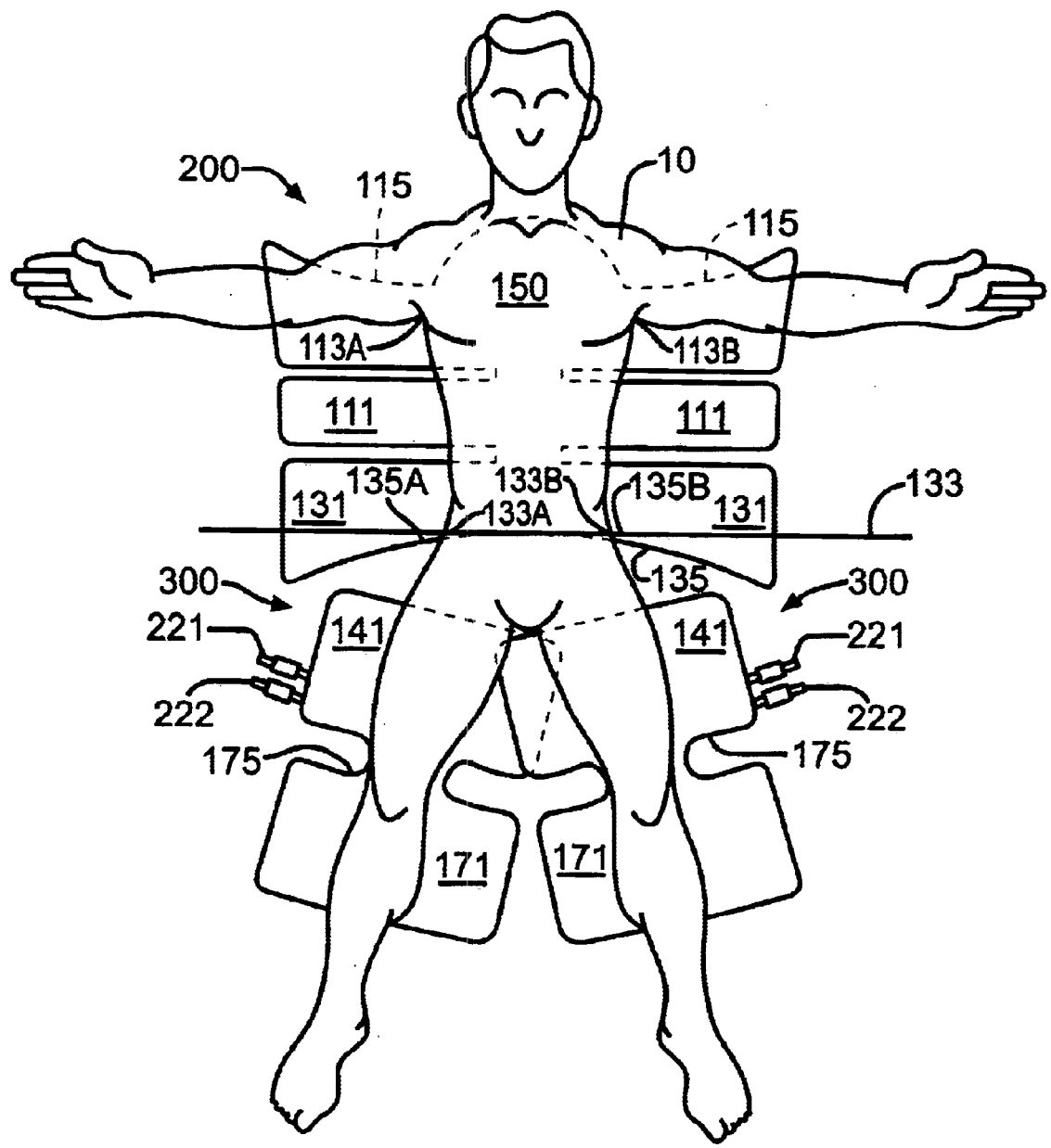
FIG. 8 is an illustration of patient 10 positioned on the heating and cooling blanket 200 and on the heating and cooling blankets 300 of the present invention, where leg wraps 300 are independent of each other and of torso wrap 200.

Referring now to FIG. 8 there is shown another embodiment of heating and cooling blankets 200 and 300 of the present invention. Cooling blanket 200 contains chest panels 111 and abdomen panel 131 connected to main panel 150 and provides for the wrapping of the chest and abdomen. Cooling blanket 300 contains a lower leg panel 171 connected via knee opening 175 to an upper leg panel 141 and provides for the wrapping of a leg with no contact or pressure point of the blanket on the knee. Knee opening 175 may be of any suitable shape. Non-limiting examples of suitable shapes for the knee opening 175 include circular, oval, rectangular, square, any n-sided regular of irregular geometric shape, or a combination thereof.

Figure 3:
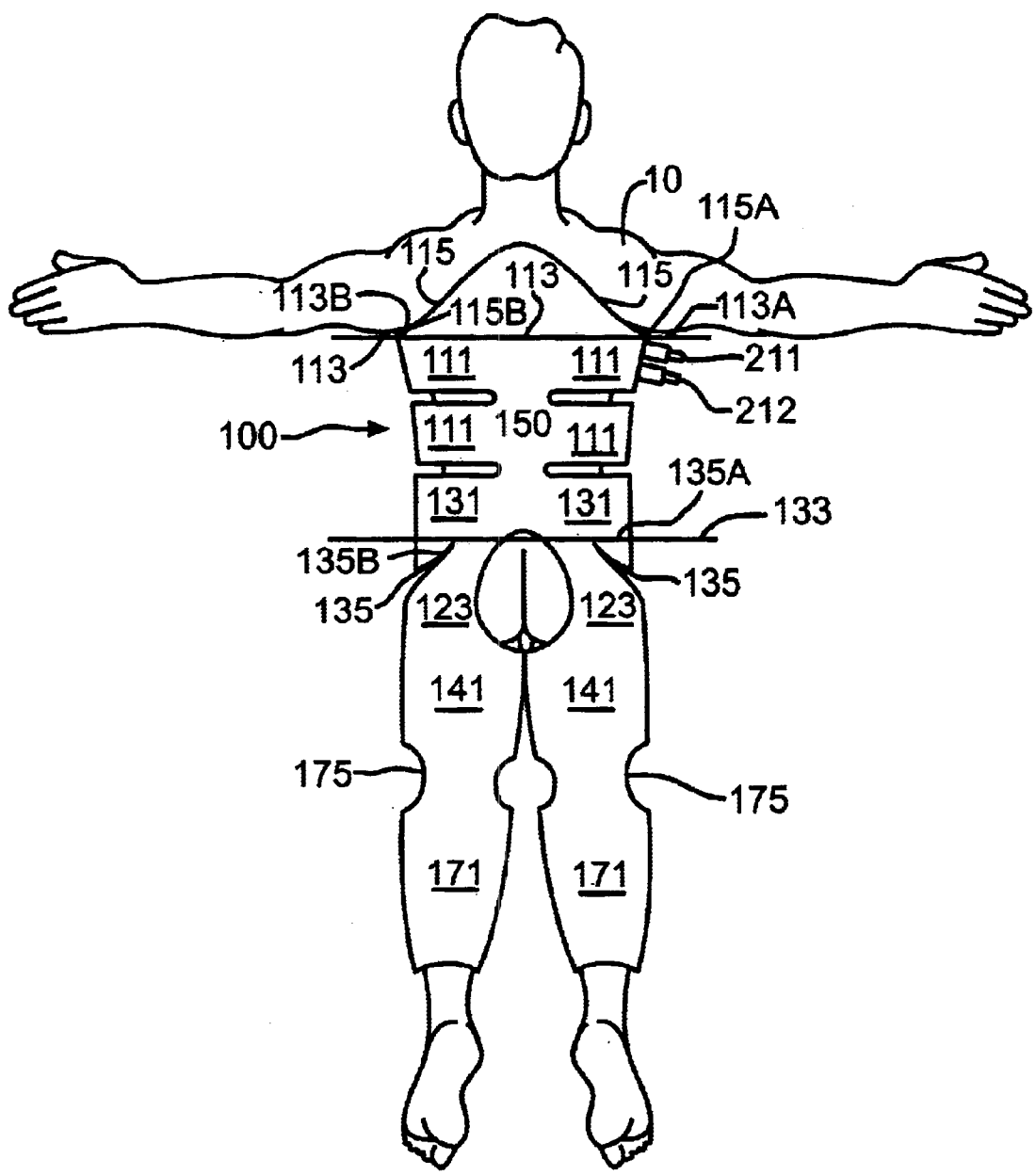
FIG. 3 is an illustration showing back view of the patient 10 positioned on the heating and cooling blanket 100 with the main panel 150, the chest panels 111, the abdomen panels 131, the upper leg panels 141 and the lower leg panels 171 wrapping respectively, the chest, abdomen, and upper and lower legs with a connecting area 123 and a cutout portion 175.

Referring now additionally to FIG. 3 there is shown an illustration showing a back view of the patient 10 positioned on the heating and cooling blanket 100 with the chest panels 111, the abdomen panels 131, the upper leg panels 141 and the lower leg panels 171 wrapping, respectively, the chest, abdomen, and upper and lower legs with the connecting area 123 and portions 115 and 175. In this view, all panels 111, 131, 141 and 171 of the blanket 100 are closed thereby providing maximum coverage of the body surface area during such time when surgical or medical access is not required for patient care. The present embodiment can also have the panels of the blanket 100 overlap each other (not shown.)

Figure 4:
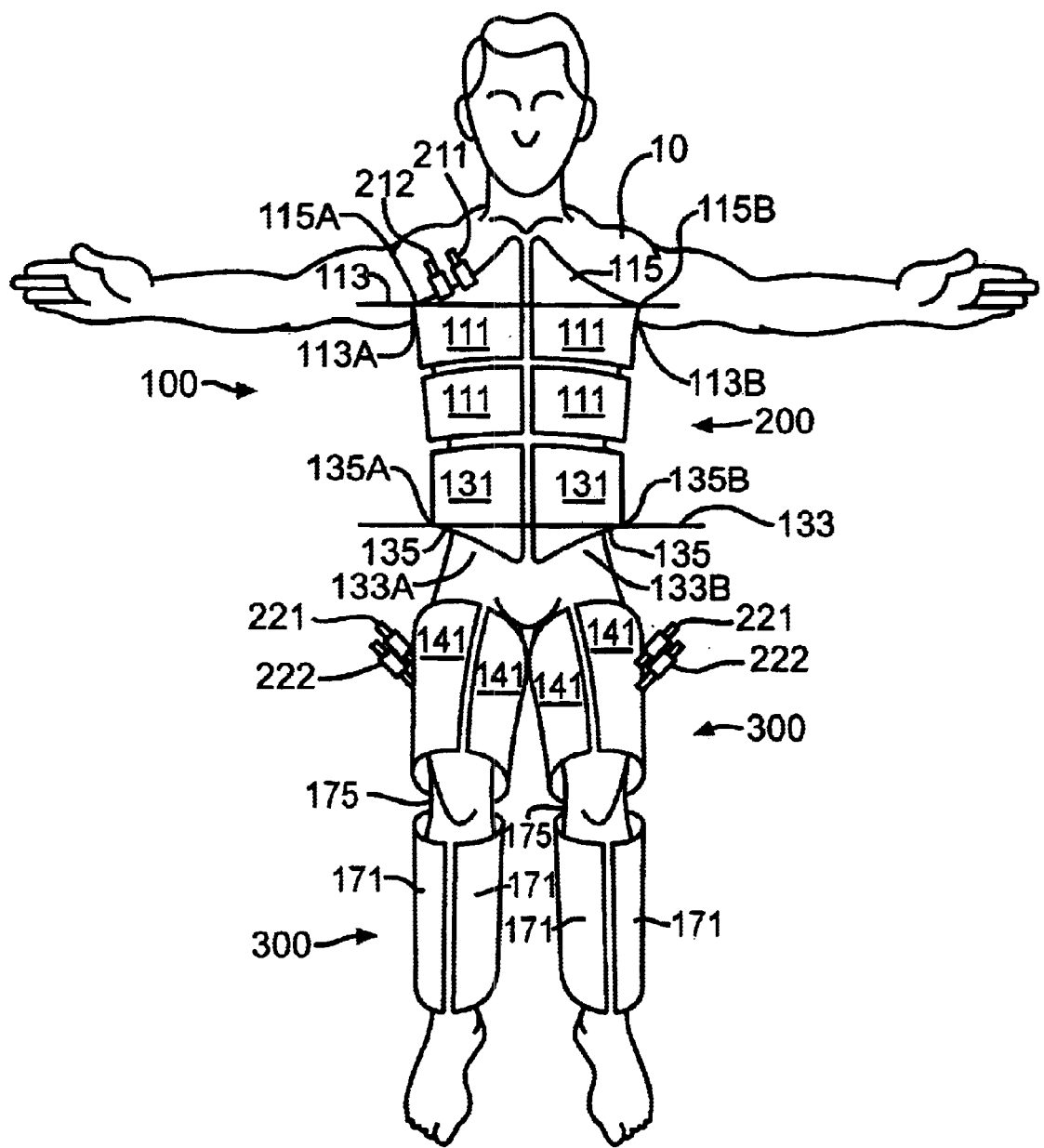
FIG. 4 is an illustration showing a front view of blanket 100 or in another embodiment, front view of blankets 200 and 300 (illustrated in FIG. 8) with the patient 10 positioned on blankets 100 and 200 with the chest panels 111, the abdomen panels 131, the upper leg panels 141 and the lower leg panels 171 with all panels closed.

Referring now to FIG. 4 there is shown an illustration showing a front view of the blanket 100 or a front view of the blankets 200 and 300 (illustrated in FIG. 8) with the patient 10 positioned on either single blanket 100 or on separate blankets 200 and 300 with the chest panels 111, the abdomen panels 131, the upper leg panels 141 and the lower leg panels 171. In this view, all the panels 111, 131, 141 and 171 of the blanket 100 or of blankets 200 and 300 are closed thereby providing maximum coverage of the body surface area during such time when surgical or medical access is not required for patient care. Note that a portion 175 allows closure of panels 141 and 171 with no contact or pressure point of the blanket on the knee or knees, and simultaneously the panels can overlap each other.

Figure 5:
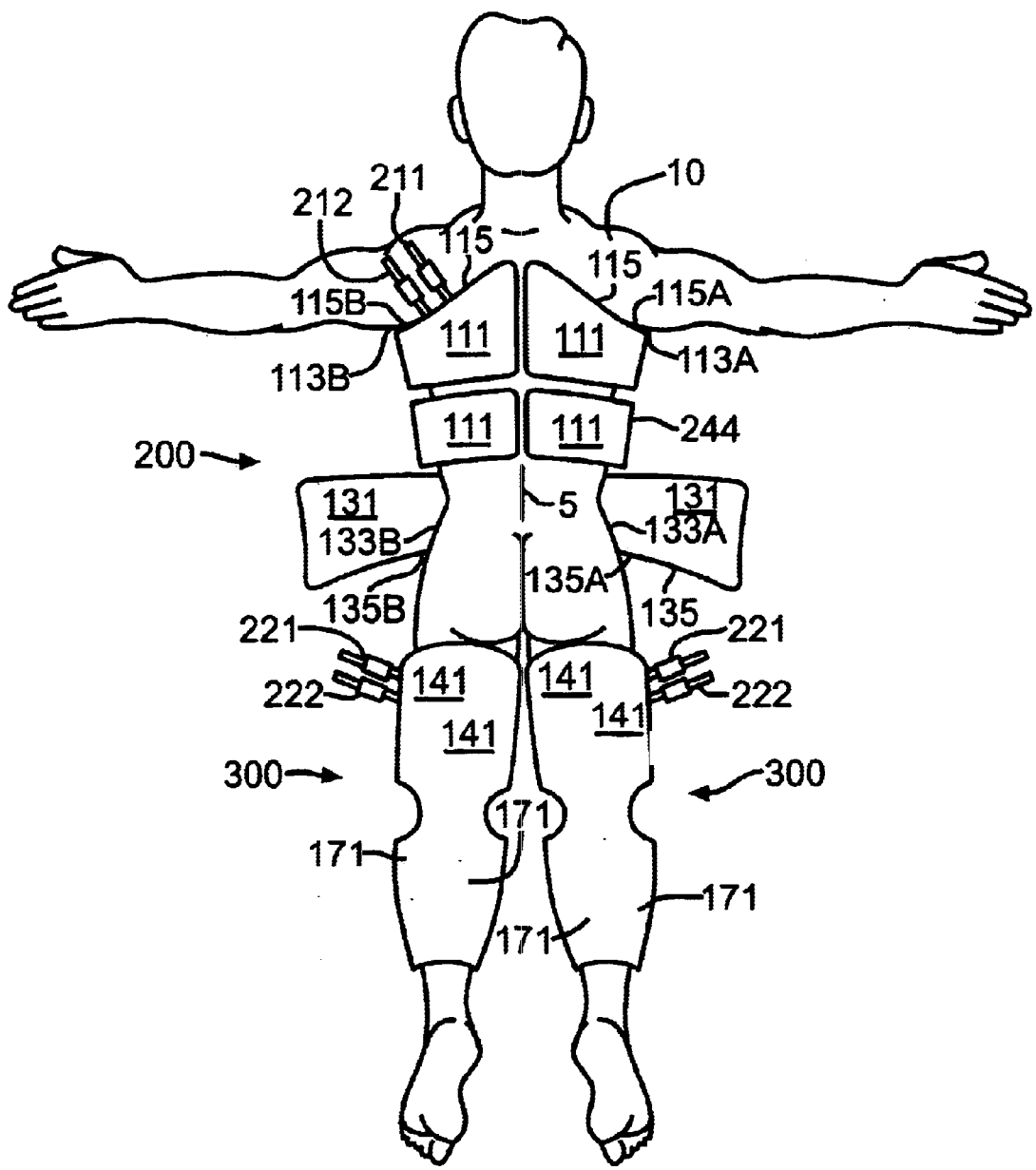
FIG. 5 is an illustration showing patient 10 in the prone position on the heating and cooling blankets 200 and 300 with the abdomen panels 131 opened to allow for surgical access to the patient's back 5. Blanket 200 is reversed so the main panel 150 is anterior to the patient 10 which permits the abdomen panel 131 to be open for surgical access to the back as illustrated.

Referring now to FIG. 5, there is shown an illustration of the patient 10 in the prone position on the heating and cooling blankets 200 and 300 with the abdomen panels 131 opened to allow for surgical access to the patient's back 5. Blanket 200 is reversed and a surgical incision is illustrated. Receiving area or main panel 150 (illustrated in FIG. 8) receives the anterior of the patient 10 so that the panels 111 and 131 of the blanket 200 open on the posterior surface of the patient 10. Placing the patient 10 on the blanket 200 in this way provides for surgical exposure of the back when the patient 10 is in the prone position while providing maximal contact of patient 10 body surface with the heating/cooling blanket 200 during surgery. Note that in FIG. 5, the blankets 300 are placed such that panels 141 and 171 open anteriorly thereby preventing pressure points on the knee or knees.

Figure 6:
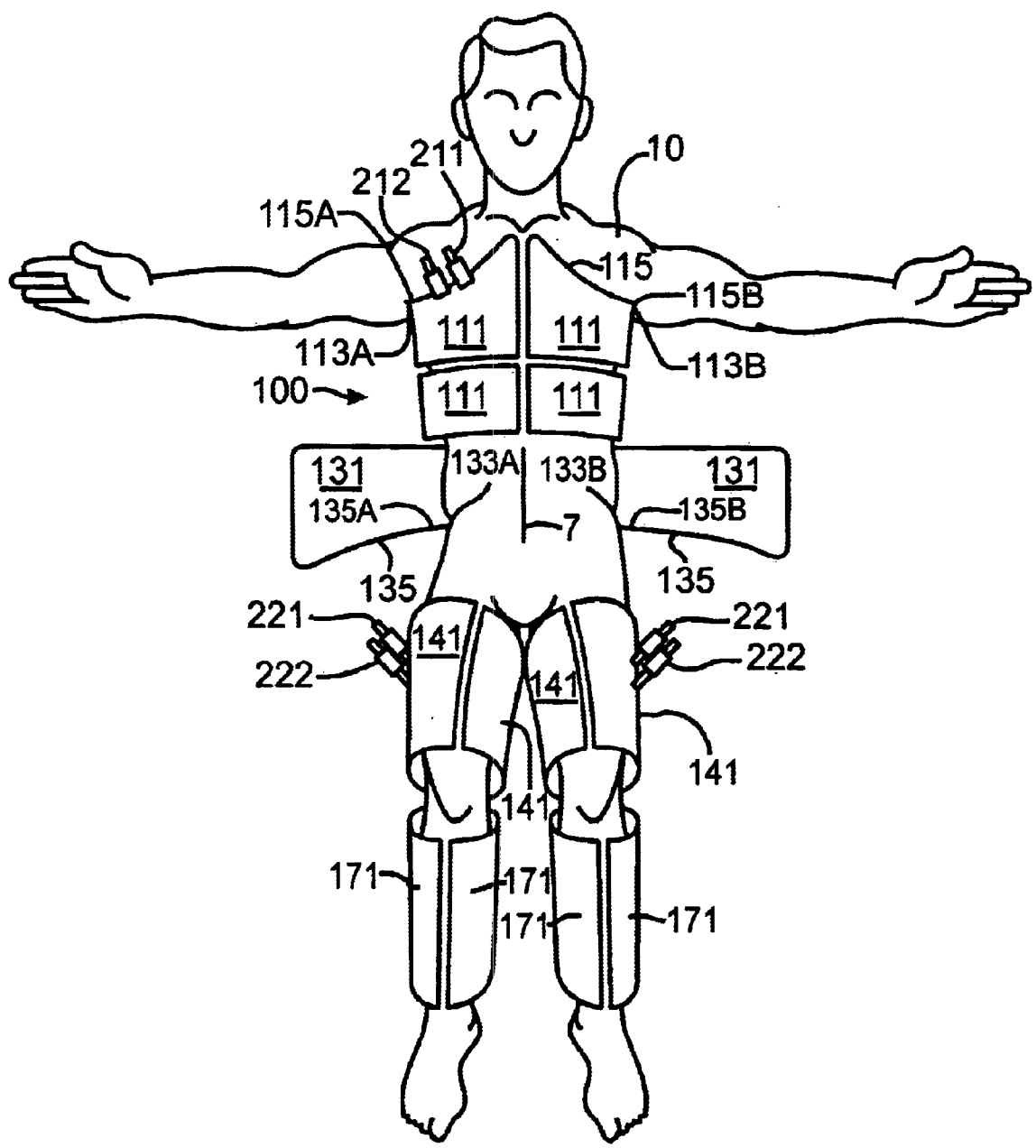
FIG. 6 is an illustration showing the patient 10 positioned on the heating and cooling blankets 100 or 200 and 300 with abdomen panels 131 opened to allow for surgical access to patient's abdomen 7. Connecting panel 123 of the blanket 100 and the main panel of the blankets 100 and 200 are not visible in this orientation.

Referring now to FIG. 6, there is shown an illustration of the patient 10 positioned on the single heating and cooling blanket 100 or on the separate heating and cooling blankets 200 and 300 with abdomen panels 131 opened to allow for surgical access to the patient's abdomen 7. Placing the patient 10 on the blanket 100 or on the blankets 200 and 300 in this position provides access to the abdomen 7, with a representative surgical incision, by opening only panel 131. Placing the patient 10 on the blanket 100 or on the blankets 200 and 300 in this way provides for surgical exposure to the abdomen 7 when the patient 10 is in the supine position, while providing maximal contact of patient 10 body surface with the heating/cooling blanket 100 or the blankets 200 and/or 300 during surgery.

Figure 7:
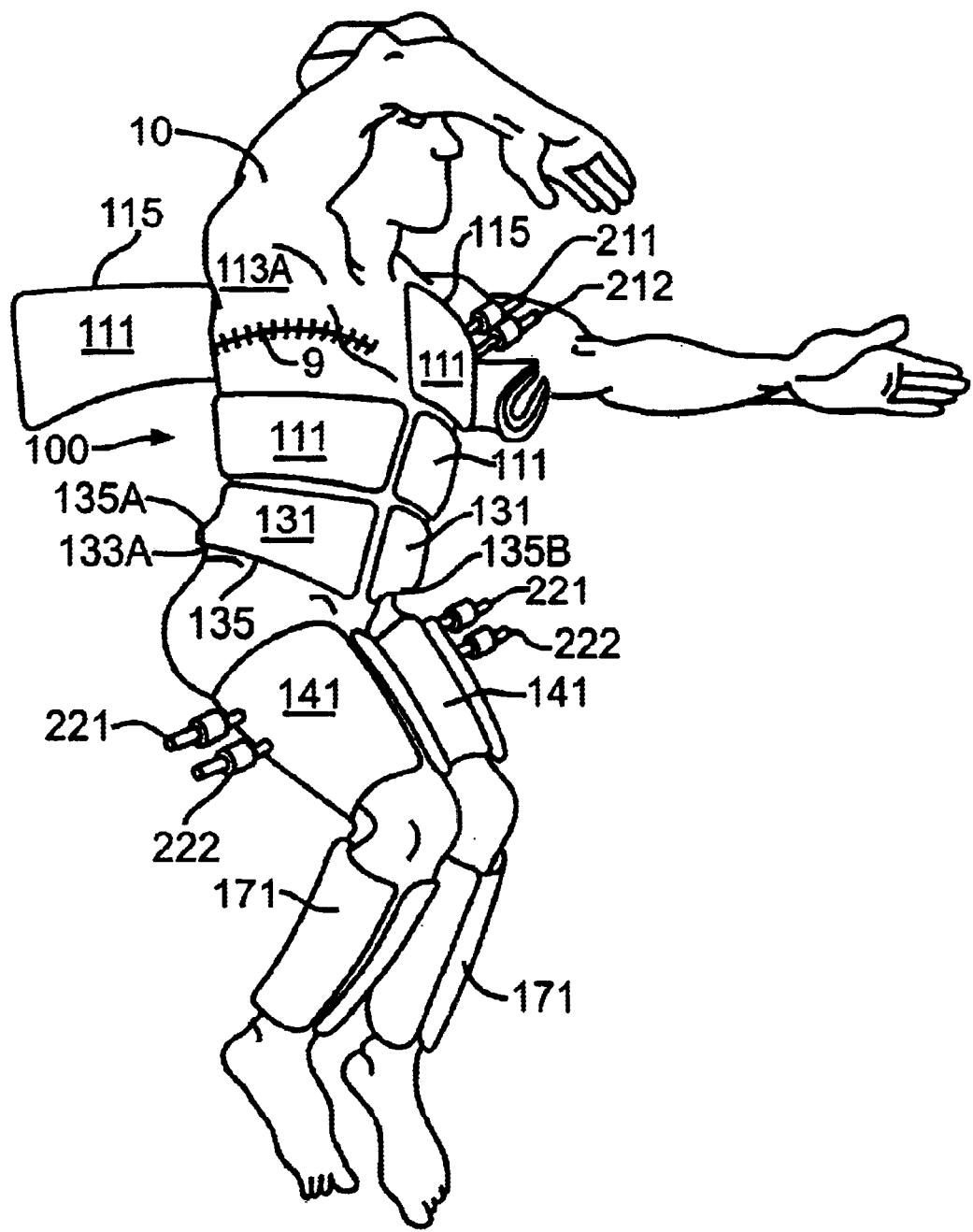
FIG. 7 is an illustration showing the patient 10 in a lateral position on the heating and cooling blankets 100 or 200 and 300 with chest panel 111 open to expose the upper right portion of the patient's chest 9. Main panel 150 (not seen) permits chest panel 111 to be opened to expose the spine of patient 10 for surgical access.

Referring now to FIG. 7, there is shown an illustration of the patient 10 in a lateral position on the heating and cooling blanket 100 or on the blankets 200 and 300 with the chest panel 111 open to expose the upper right portion of the patient's chest 9. Preferably, the central panel 150 as shown in FIGS. 2 and 8, must be narrow enough that the thoracic incision may be carried well posteriorly. Unique to the heating and cooling blankets of the present invention, maximum contact between the blankets and the body surface of the patient 10 is effectuated even when the patient 10 is in the lateral position. Prior art blanket B would only contact lateral aspect of the dependent portion of the body with the patient 10 in the same position.

Referring now to FIG. 8, there is shown an illustration of the patient 10 positioned on the heating and cooling blanket 200 and on the heating and cooling blankets 300 of the present invention with all panels open.

Figure 9:
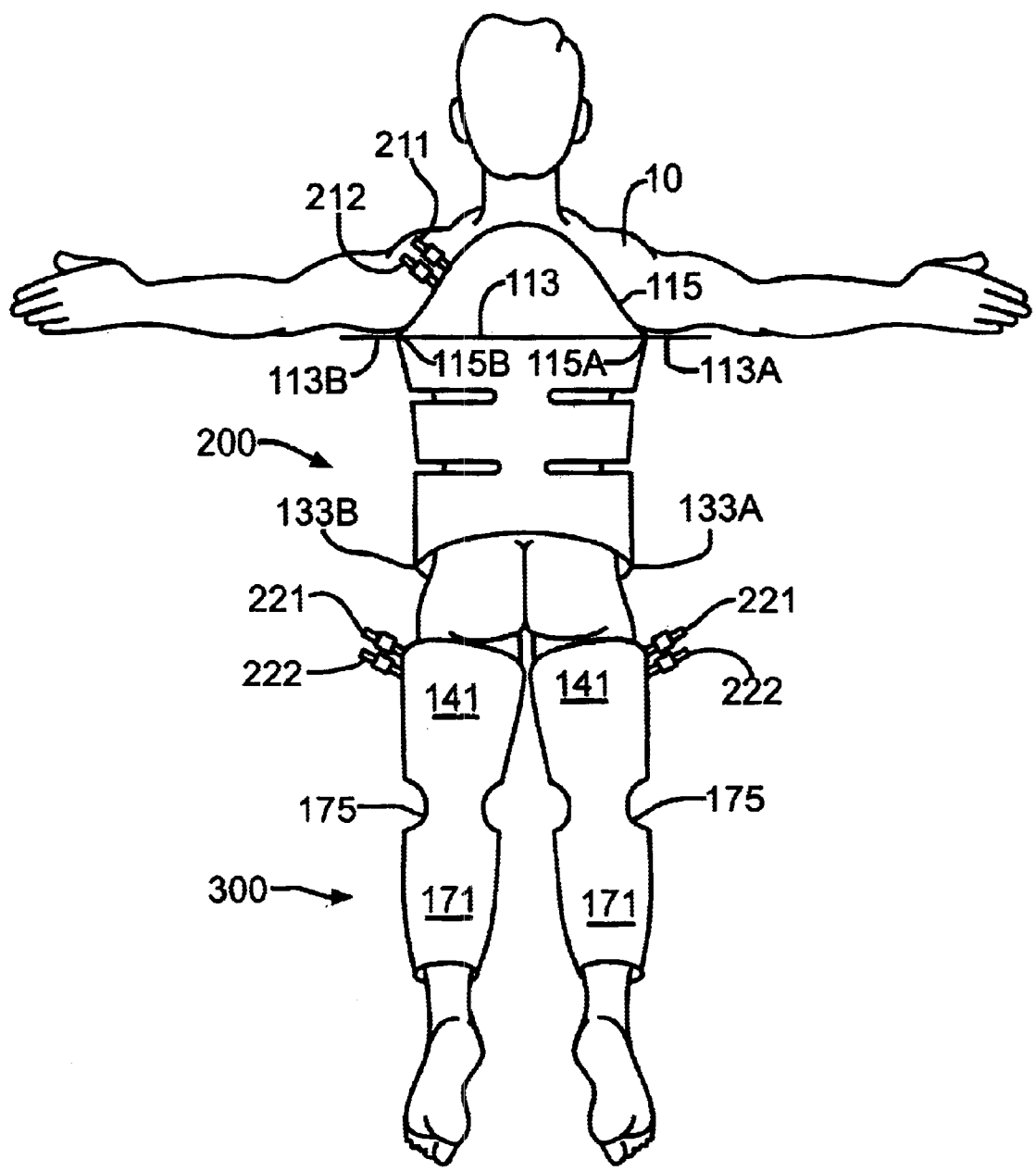
FIG. 9 is an illustration showing a back view of patient 10 positioned on the heating and cooling blankets 200 and 300 of FIG. 8. The anterior view of FIG. 9 is the same as shown in FIG. 4

Referring now to FIG. 9, there is shown an illustration of the patient 10 positioned on the heating and cooling blanket 200 and the blankets 300 of FIG. 8. The anterior view of FIG. 9 is the same as shown in FIG. 4.

Figure 10:
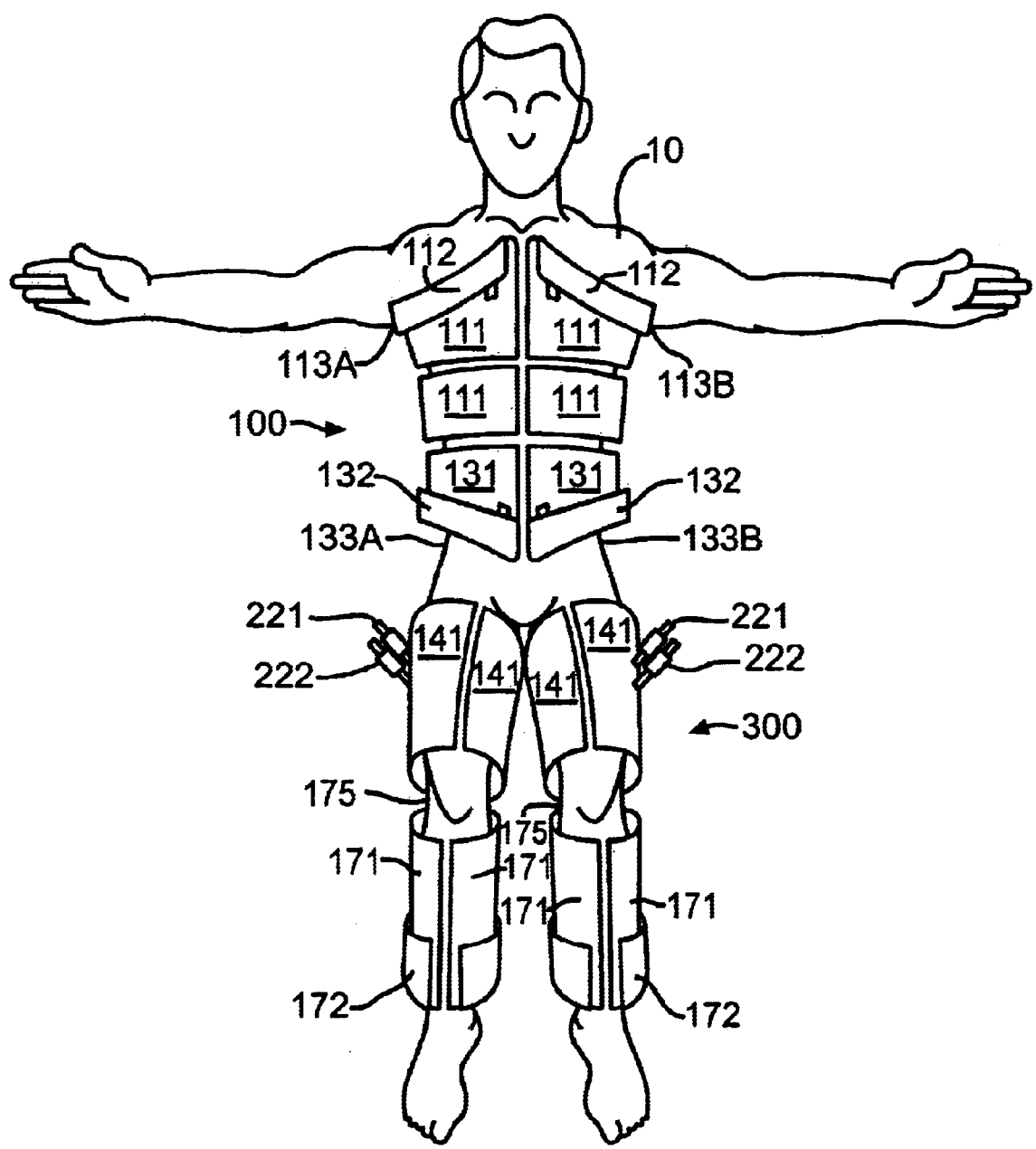
FIG. 10 is an illustration showing the front view of patient 10 positioned on the heating and cooling blanket 100 or on blankets 200 and 300 with the chest panels 111 having extensions 112, the abdomen panels 131 having extensions 132, the upper leg panels 141 and the lower leg panels 171 having extensions 172 wrapping, respectively, the chest, the abdomen, and the upper and lower legs.

Referring now to FIG. 10 is an illustration showing the front view of the patient 10 positioned on the heating and cooling blanket 100 or on the blankets 200 and 300 with the chest panels 111 having extensions 112, the abdomen panels 131 having extensions 132, the upper leg panels 141 and the lower leg panels 171 having extensions 172, wrapping, respectively, the chest, the abdomen, and the upper and lower legs. Extensions 172 could be positioned on the superior portion of the panel 141 or on the inferior portion of 171.

Figure 11:
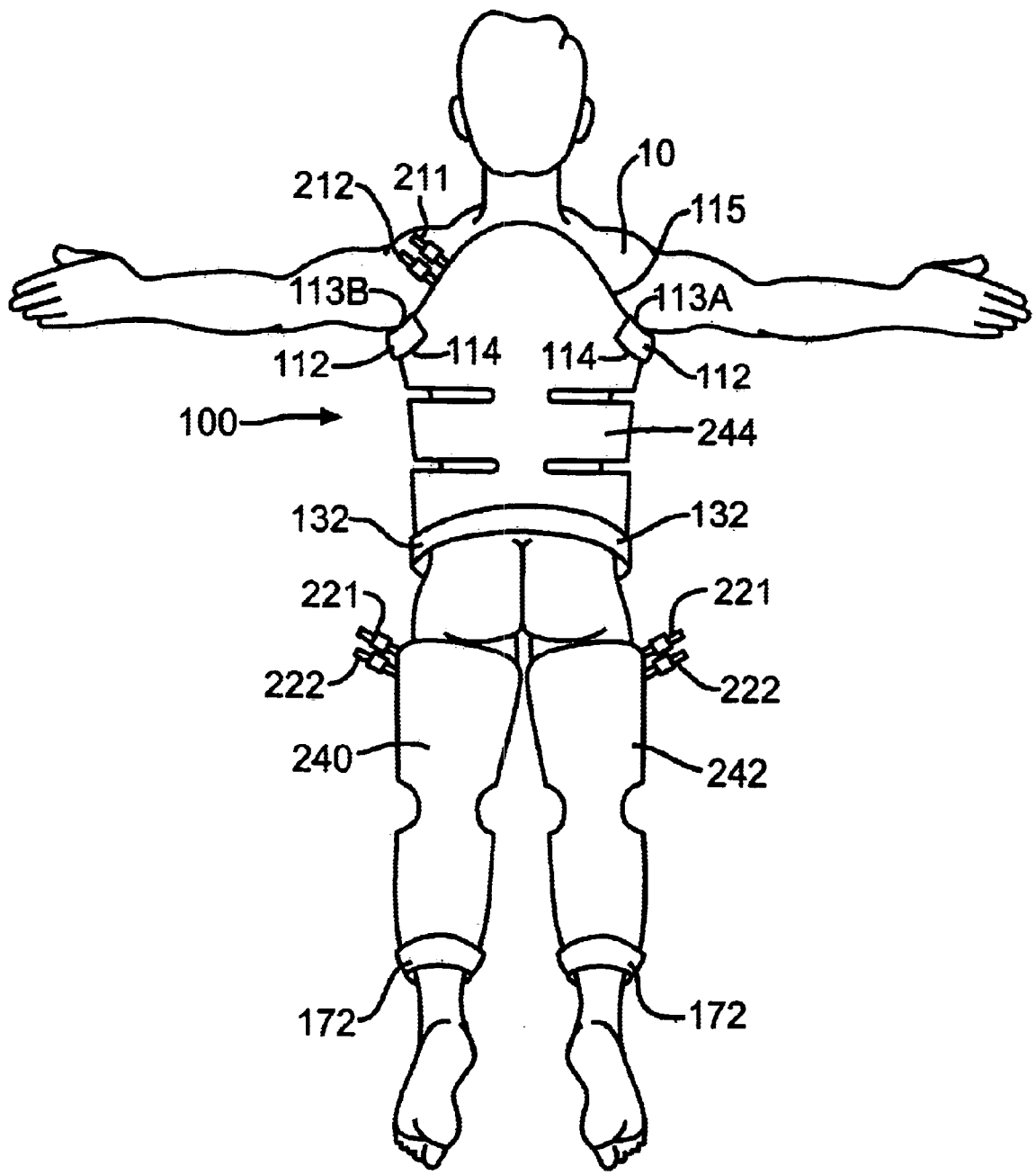
FIG. 11 is an illustration showing the back view of patient 10 positioned on heating and cooling blankets 200 and 300 with chest panels 111, having extensions 112, abdomen panels 131 having extensions 132, upper leg panels 141 and lower leg panels 171 having extensions 172 wrapping respectively, the chest, abdomen, and upper and lower legs.

Referring now to FIG. 11, there is shown an illustration showing the back view of the patient 10 positioned on one embodiment of the heating and cooling blankets 200 and 300.

Optional extension panels 112, 132, and 172 permit one size of the blanket 100 or the blankets 200 and 300 to fit a wider range of body sizes. For example, as shown in FIGS. 10 and 11, for smaller persons, panels 112, 132, and 172 are folded or rolled upwards and are secured in place by their own weight or optionally by fasteners (including snaps, buttons, hooks, zippers, and hook and loop type systems a commercially available example which includes VELCRO®).

Notice that the blankets of the present invention provide full access to the head and neck, the arms, the feet, and the perineum. Although not necessary, it is desirable that the heating and cooling blankets 100, 200 and 300 be reversible, that is, that patient 10 may be placed on either surface of blankets 100, 200 or 300.

Referring to FIG. 2 and FIG. 8, main panel 150 is provided so that in the lateral position during surgery the heating and cooling blanket 100 or 200 may optionally be used with one or more panels opened, providing full access to the thorax and the flanks for surgery. The main panel 150 generally extends from the neck to the buttocks and is bounded by fold lines 151 and 152 (only seen in FIG. 2), with the distance between fold lines in the range of about 2 to about 12 inches, preferably in the range of about 8 to about 12 inches.

Referring now additionally to FIGS. 2, 3 and 8, the purpose of the central or main panel 150 is also to provide an attachment locations for the panels 111 and panels 131 such that the slight gap between the panels allows the panels 111 or 131 to be independently opened without obstructing surgical access to the lateral portion of the chest or of the flank. This feature allows select surgical access to the chest and/or the abdomen while the patient 10 is in the lateral, prone and supine positions while still providing for maximum coverage of the patient 10.

It is generally desirable to provide for spacing between the chest panels 111 and the abdomen panels 131, to allow for access to the abdomen during laparotomy. While in the embodiment as shown, only the upper edge of the chest panels 111 are tapered, this may be accomplished by providing one or both of the panels 111 and 131 with a slight taper or angle to provide for spacing between panels 111 and 131.

Preferably, to provide coverage to a larger surface area of the body, the panel 111 may contain one or more axillary curvilinear portions 115, as shown in the figures such that when panel 111 encircles the body, the one or more curvilinear portions 115 define axillary cradles 115A and 115B positioned under and adjacent to axillae 113A and 113B such that at least a portion of panel 111 extends above line 113 drawn between the axillae 113A and 113B as illustrated in FIGS. 2–4 and 9. In addition, panel 131 may contain one or more ilia curvilinear portions 135 such that when panel 131 encircles the body, the one or more curvilinear portions 135 define ilia saddles 135A and 135B positioned above and adjacent to the iliac crest 133A and 133B such that at least a portion of the panel 131 extends below line 133 drawn between the iliac crest 133A and 133B as illustrated in FIGS. 2, 3, 4 and 8. Although the cradles 115A and 115B and saddles 135A and 135B are generally defined as curvilinear in shape, it is understood that they may be any suitable shape or cut out portion to receive the axillae and ilia respectively. Non-limiting examples of suitable shapes for cradles 115A and 115B and for saddles 135A and 135B included square, rectangular, oval, any regular or irregular geometric shape, or a combination thereof.

As shown in FIG. 2, the perineum opening 82 of blanket 100 provides both anterior and posterior access at the perineum for hygiene and for catheter egress. Alternatively, the heating and cooling blanket 100 and 200, may be provided with a disposable surface at the perineum to prevent soiling of the blanket 100.

The heating and cooling apparati 100, 200 and 300 may be provided with a heat transfer fluid, generally an alcohol or an aqueous solution, to allow for heating or cooling. Generally, a heat transfer liquid fluid, most commonly water, is circulated through the heating and cooling blanket 100, 200 or 300 which is generally provided with internal passages, tubing, channels or the like. This heat transfer fluid is provided at a desired temperature, and is circulated at a desired rate to provide the desired heating or cooling to the patient 10.

Each section of the heating and cooling blanket 100 (leg and chest areas), and the entire portion of each blanket 200 or 300 consists of a single fluid communication zone. Such an arrangement would provide essentially a single temperature throughout the blankets 200, 300 or the sections of the blanket 100, with minor temperature deviations depending upon the fluid flow patterns.

As stated above, the heating and cooling blanket 100 has two distinct areas, the first being the leg area, and the second being the chest area. Each area has its own fluid communication zone so they can be independently heated and/or cooled as desired. For example, fluid to main panel 150 would be provided through connectors 211 and 212 for this application. Fluid to leg panels 141 and 171 would be provided through connectors 221 and 222 in this application.

Each fluid communication zone is to be heated and/or cooled through internal channels, passages tubing or the like, for receiving a transfer medium which will be passed through the zone to provide heating or cooling. For example, the heating and cooling zones may be provided with one or more medium carrying conduits through which a heat transfer medium can flow. Alternatively, each of the heat transfer zones, may be provided with a plurality of passages forming a crisscross waffle grid pattern for the random flow of the heat transfer medium in many directions within each of the heat transfer zones as is disclosed in U.S. Pat. No. 4,149,541, issued Apr. 17, 1979 to Gammons et al., the disclosure of which is herein incorporated by reference.

The various fluid communication zones of the heating and cooling apparati 100, 200 and 300 include a heat transfer inlet for introducing the heat transfer medium to the respective zone, and a heat transfer medium outlet through which the heat transfer medium exits the respective heating and cooling blanket. Generally, the heat transfer medium inlet and the heat transfer medium outlet comprise a screw fit, snap fit or other type of friction fit mechanism for engagement with tubing, piping, hosing or other type of conduit which will provide a heat transfer medium to the heat transfer zone and carry such heat transfer medium away from the heat transfer zone.

It is generally desired that at least one set of heat transfer medium inlets and the heat transfer medium outlets be positioned on one side of the heating and cooling blankets 100, 200 or 300, because generally, the direction from which the fluid is provided will generally also be the direction for return. Preferably, at least one set of heat transfer medium inlets and the heat transfer medium outlets are positioned on each side of the heating and cooling the blankets 100, 200 or 300 because generally in the haste of positioning the blankets 100, 200 or 300, care may not have been taken to determine the locations of the source of heat transfer fluid.

For example, in the embodiments as shown in FIGS. 2–5, the upper body chest panels 111 and the abdomen panels 131 are in fluid communication with each other with the heat transfer fluid provided through the tubing 211 and returning through the tubing 212. The heat transfer fluid enters through the tubing 211, circulates through the body chest panels 111 and the abdomen panels 131, and returns through the tubing 212. Likewise, lower body upper leg panels 141 and lower leg panels 171 are in communication with each other. Heat transfer fluid enters through the tubing 221, circulates through the panels 141 and 171 and returns through the tubing 222. The blankets 200 and 300 may be connected to each through an external source of fluid or the connectors 221 and 222 may be connected to each other with an additional set of hoses entering one blanket 300 which then connects to an external fluid source. In addition, the blankets 200 and 300 may be blankets having different medium sources. Slightly different, non-limiting alternative positioning embodiments for tubing 211 and 212 and tubing 221 and 222 are shown in FIGS. 2–7.

It is also generally desirable that the internal fluid communication of blankets 100, 200 and 300 be suitable to allow for panels and panel extensions to be folded back on themselves without substantially impeding fluid flow.

As an alternate mode of operating the heating and cooling blanket embodiment as shown in FIGS. 2–4, the outlet tubing 212 could be connected with the inlet tubing 221 to convert this two zone embodiment into a single fluid communication zone embodiment.

In the practice of the present invention, the heat transfer medium utilized may be any suitable liquid, gas, gel, foam, emulsion or other flowable medium which is suitable for heat transfer. Preferably, the heat transfer medium utilized in the present invention is an aqueous solution (like water) or an alcohol. It should be understood that the heat transfer medium utilized in the present invention may include other substances, such as preservatives, bacteriacides, odorants, coloring agents, anti-corrosion agents, anti-oxidants, surfactants, sealants, and the like.

Heating and cooling apparati 100, 200 and 300 may optionally be provided by one or more access points for gaining access to a specific portion of the body of patient 10. For example, any of the panels or optional panel extensions may be provided with smaller sized openable or removable panels to allow access to the patient 10 without the need to open or remove the larger panel. Each of these smaller sized panels may be secured in place by their own weight, with adhesive tape, or by any suitable fastener including snaps, buttons, hooks, zippers, and hook and loop type systems a commercially available example which includes VEL-CRO.®

Optionally, any part of heating and cooling blanket 100, 200 or 300 may be transparent to permit visual observation of the underlying body without removal of the blanket 100, 200 or 300.

The heat transfer medium of the present invention may be circulated through a closed loop heating or cooling system which is positioned adjacent to the heating and cooling apparati 100, 200 or 300. Methods of an apparatus for heating and cooling a circulating heat transfer medium are well known, and the present invention is not to be limited in any particular type of system. Alternatively, heat transfer medium may be provided from a larger system, such as a hospital heating or cooling water system.

It is envisioned that any suitable materials of construction may be utilized in the construction of the heating and cooling apparati 100, 200 or 300 of the present invention. In most instances, the range of operating temperatures will be those that which water is in the liquid state. It is generally preferred that the material of construction not be too resistant to bending and folding at colder temperatures. In general, the materials of construction will generally be selected from among thermoplastics, thermosets, elastomers, and rubbers.

The surface of heating and cooling blankets 100, 200 or 300 which contacts patient 10 preferably comprises a conventional absorbent material to absorb or remove perspiration from a patient.

It must be understood that while the heating and cooling blankets of the present invention have been illustrated only with panels for the chest, abdomen, and upper and lower legs, other panels for the head, neck, arms, hands and feet may optionally be utilized as desired or needed. Additionally, any suitable combination of panels covering any desired portion(s) of the patient 10 may be utilized.

Alternative embodiment of the present invention are illustrated in FIGS. 12a–r. In particular, FIGS. 12a and 12b(i) and b(ii) illustrate the two distinct methods that the torso blanket can be made. As shown in FIG. 12a, the torso blanket 200 can be cut in one material with the requisite shape(s) 800, 802, 804 to extend beyond the patient's 10 axillary line or iliac line 113 and 133. From this initial cut, the material is folded at line 806 to form fold seam 818, and then the material is connected together at three seams, a first perimeter seam 810, a second perimeter seam 812, and a third perimeter seam 814. The connection process can occur by various conventional methods, which include, and are not limited to, heat welding, sonic welding, and adhesives. An example of such blankets 200 are illustrated in FIGS. 12d, e, f, g, h, and i. Alternatively, the fold seam 818 can be connected together to form a fourth perimeter seam 816, as illustrated in FIGS. 12, c, j, and k.

The first perimeter seam 810, the second perimeter seam 812, the third perimeter seam 814, and the fold seam 818 (and the first perimeter seam 810, the second perimeter seam 812, the third perimeter seam 814, and the fourth perimeter seam 816) are the outer perimeter of a liquid circulation area 820. As stated previously, the liquid circulation area 820 receives a liquid medium through an inlet 822, the liquid circulates within the area 820, and then the liquid is released through the outlet 824, as only shown in FIG. 12c but found in each embodiment.

As illustrated, there are no panels in the torso blanket as shown in FIGS. 12a–f and h–j. There are no panels because that diminishes the chances of any leakage of the medium fluid from the torso blanket.

If panels are to be used, then the torso blanket has at least a fifth perimeter seam 826, and a split 828 along the fifth perimeter seam 826, as shown in FIGS. 12g and k. The fifth perimeter seam 826 is created in the same method as the first, second, third and fourth perimeter seams. The split 828 is generated by a conventional method to cut material, like scissors or a sharp object.

When the torso blanket is to extend beyond the patient's 10 axillary line and iliac line, then the second perimeter seam 812 is opposite the first perimeter seam 810 in relation to the blanket, as shown in FIGS. 12d, i, j, and k. Otherwise, the relative position of the first, second and third perimeter seams is relative.

Turning to FIGS. 12b(i) and (ii), this illustration shows an alternative method to make the torso blanket. This method requires the material be cut into two mirror images. From this initial cut, the material is folded at line 806 to form fold seam 818, so that two mirror image surfaces oppose each other, one on top and one on the bottom.

FIGS. 12l–r illustrate the methods to form the leg panel 300. The leg panel, as shown in FIGS. 12l and m, can be cut in one material with the requisite shape opening 840 for a patient's knee. From this initial cut, the material is folded at line 806 to form fold seam 818, and then the material is connected together at three seams, a first perimeter seam 810, a second perimeter seam 812, and a third perimeter seam 814. The connection process can occur by various conventional methods, which include, and are not limited to, heat welding, sonic welding, and adhesives. An example of such blankets 300 are illustrated in FIGS. 12n, p and q. Alternatively, the fold seam 818 can be connected together to form a fourth perimeter seam 816, as illustrated in FIGS. 12r and o.

Similarly, the leg blanket has the first perimeter seam 810, the second perimeter seam 812, the third perimeter seam 814, and the fold seam 818 (and the first perimeter seam 810, the second perimeter seam 812, the third perimeter seam 814, and the fourth perimeter seam 816) form the outer perimeter of a liquid circulation area 820. As stated previously, the liquid circulation area 820 receives a liquid medium through an inlet 872, the liquid circulates within the area 870, and then the liquid is released through the outlet 874, as only shown in FIG. 12n for the leg blanket design but found in each leg blanket embodiment.

Alternatively, the leg blanket can be formed from material when the material is cut into two mirror images, and then put together by at least having four perimeter seams, as shown in FIGS. 12o and r.

The present invention can have the torso blanket 200 and the leg blanket 300 provide the desired temperature to the patient 10 by various methods. The first method is illustrated in FIG. 13a, which illustrates a liquid medium source 860 that provides the desired liquid medium at a desired temperature to the inlet 822. The liquid medium circulates within the liquid circulation area 820. Once fully circulated, the liquid medium exits through outlet 824. From outlet 824, the liquid medium is directed into inlet 872. From inlet 872, the liquid medium is directed into liquid circulation area 870. From there, the liquid medium escapes out of the area 870 by outlet 874. The liquid medium should never contact the patient 10.

The inverse of this method illustrated in FIG. 13a is illustrated in FIG. 13d. In either embodiment, the liquid medium in the blankets 200, 300 are the same. The temperatures, however, may be the same or different.

Alternatively, FIG. 13b illustrates a method wherein the liquid medium source 860 provides the desired liquid medium at a desired temperature directly to the inlet 822, and inlet 872. The liquid medium circulates within the respective liquid circulation area 820, 870. Once fully circulated, the liquid medium exits through respective outlet 824, 874. From each outlet, the liquid medium escapes out of the blankets. The liquid medium should never contact the patient 10.

In another embodiment illustrated in FIG. 13c, each blanket 200, 300 has its own liquid medium source 860, 861 that provides a desired liquid medium at a desired temperature to the respective inlet 822, 872. The respective liquid medium circulates through its respective liquid circulation area 820, 870 and out its respective outlet 824, 874. In this embodiment, the liquid mediums can be the same or different mediums, and the same or different temperatures.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

We claim:

1. An apparatus for applying a desired temperature to a human body having a torso, at least one leg having a knee, an axillae, and an ilia, with an axillary line defined as running between the axillae, and with an iliac line defined as running between the ilia, the apparatus comprising:

(a) a torso blanket having a first perimeter seam, a second perimeter seam, a third perimeter seam and a liquid circulation area, and the liquid circulation area is capable of and suitable for encircling the torso;

(b) the first perimeter seam is shaped to receive the axillae so a portion of the torso blanket extends above the axillary line; and (c) a single first fluid circulation system that allows a first liquid medium to circulate within the liquid circulation area in such a manner to effectively transfer the desired thermal property of the first liquid medium to the human body by having the first liquid medium (i) enter the liquid circulation area through a first inlet and (ii) exit the liquid circulation area through a first outlet wherein the first outlet is not the same as the first inlet, and without the first liquid medium contacting the human body.

2. The apparatus of claim 1 wherein when the second perimeter seam is opposite the first perimeter seam, the second perimeter seam is shaped to receive the ilia so a portion of the torso blanket extends below the iliac line.

3. The apparatus of claim 2 wherein the second perimeter seam is a curvilinear shape.

4. The apparatus of claim 1 wherein the first perimeter seam is a curvilinear shape.

5. The apparatus of claim 1 further comprising a folded portion of the torso blanket that is opposite the third perimeter seam, wherein the first perimeter seam. The second perimeter seam, the third perimeter seam, and the folded portion of the torso blanket define the liquid circulation area's outer perimeter.

6. The apparatus of claim 5 wherein there is no perimeter seam extending into the liquid circulation area from the first perimeter seam, the second perimeter seam, and the third perimeter seam.

7. The apparatus of claim 1 further comprising a fourth perimeter seam that is opposite the third perimeter seam, wherein the first perimeter seam, the second perimeter seam, the third perimeter seam, and the fourth perimeter seam define the liquid circulation area's outer perimeter.

8. The apparatus of claim 7 wherein there is no perimeter seam extending into the liquid circulation area from the first perimeter seam, the second perimeter seam, the third perimeter seam, and the fourth perimeter seam.

9. The apparatus of claim 1 further comprising at least one leg panel suitable for wrapping at least one of the legs, wherein the circulation system allows th first liquid medium to (a) enter into the leg panel through a second inlet, (b) circulate within the leg panel, and (c) exit out of the leg panel through a second outlet that is distinct from the first and second inlets.

10. The apparatus of claim 9 wherein the at least one leg panel defines an opening for the knee.

11. The apparatus of claim 1 further comprising at least one leg panel suitable for wrapping at least one of the legs, wherein a second circulation system allows a second liquid medium to (a) enter into the leg panel through a second inlet, (b) circulate within the leg panel, and (c) exit out of the leg panel through a second outlet that is distinct from the first and second inlets.

12. The apparatus of claim 11 wherein the second liquid medium is the same as the first liquid medium.

13. The apparatus of claim 12 wherein the first liquid medium and the second liquid medium have different temperatures.

14. The apparatus of claim 12 wherein the first liquid medium and the second liquid medium have the same temperature.

15. The apparatus of claim 11 wherein the first liquid medium and the second liquid medium are different liquids.

16. The apparatus of claim 15 wherein the first liquid medium and the second liquid medium have different temperatures.

17. The apparatus of claim 15 wherein the first liquid medium and the second liquid medium have the same temperature.

18. The apparatus of claim 11 wherein the at least one leg panel defines an opening for the knee.

19. The apparatus of claim 1 wherein the torso blanket has a fifth perimeter seam that extends from the third perimeter seam into the liquid circulation area.

20. The apparatus of claim 19 wherein the fifth perimeter seam is split to form at least two panels in the liquid circulation area.

21. The apparatus of claim 1 wherein the liquid circulation area may be folded to accommodate various torso sizes.

22. An apparatus for applying a desired temperature to a human body having a torso, at least one leg having a knee, an axillae, and an ilia, with an axillary line defined as running between the axillae, and with an iliac line defined as running between the ilia, the apparatus comprising:
(a) a torso blanket having a first perimeter seam, a second perimeter seam, a third perimeter seam and a liquid circulation area, and the liquid circulation area is capable of and suitable for encircling the torso;
(b) the first perimeter seam is shaped to receive the ilia so a portion of the torso blanket extends above the iliac line; and
(c) a single first fluid circulation system that allows a first liquid medium to circulate within, the liquid circulation area in such a manner to effectively transfer the desired thermal property of the first liquid medium to the human body by having the first liquid medium (i) enter the liquid circulation area through a first inlet and (ii) exit the liguid circulation area through a first outlet wherein the first outlet is not the same as the first inlet, and without the first liquid medium contacting the human body.

23. The apparatus of claim 22 wherein when the second perimeter seam is opposite the first perimeter seam, the second perimeter seam is shaped to receive the axillae so a portion of the torso blanket extends above the axillary line.

24. The apparatus of claim 23 wherein when the second perimeter seam is a curvilinear shape.

25. The apparatus of claim 22 wherein when the first perimeter seam is a curvilinear shape.

26. The apparatus of claim 22 further comprising a folded portion of the torso blanket that is opposite the third perimeter seam, wherein the first perimeter seam, the second perimeter seam, the third perimeter seam, and the folded portion of the torso blanket define the liquid circulation area's outer perimeter.

27. The apparatus of claim 22 further comprising a fourth perimeter seam that is opposite the third perimeter seam, wherein the first perimeter seam, the second perimeter seam, the third perimeter seam, and the fourth perimeter seam define the liquid circulation area's outer perimeter.

28. The apparatus of claim 22 further comprising at least one leg panel suitable for wrapping at least one of the legs, wherein the circulation system allows the first liquid medium to (a) enter into the leg panel through a second inlet, (b) circulate within the leg panel, and (c) exit out of the leg through a second outlet that is distinct from the first and second inlets.

29. The apparatus of claim 28 wherein the at least one leg panel defines an opening for the knee.

30. The apparatus of claim 22 further comprising at least one leg panel suitable for wrapping at least one of the legs, wherein a second circulation system allows a second liquid medium to (a) enter into the leg panel, (b) circulate within the leg panel, and (c) exit out of the leg panel.

31. The apparatus of claim 30 wherein the second liquid medium is the same as the first liquid medium.

32. The apparatus of claim 31 wherein the first liquid medium and the second liquid medium have different temperatures.

33. The apparatus of claim 31 wherein the first liquid medium and the second liquid medium have the same temperature.

34. The apparatus of claim 30 wherein the first liquid medium and the second liquid medium are different liquids.

35. The apparatus of claim 34 wherein the first liquid medium and the second liquid medium have different temperatures.

36. The apparatus of claim 34 wherein the first liquid medium and the second liquid medium have the same temperature.

37. The apparatus of claim 30 wherein the at least one leg panel defines an opening for the knee.

38. The apparatus of claim 22 wherein the torso blanket has a fifth perimeter seam that extends from the third perimeter seam into the liquid circulation area.

39. The apparatus of claim 38 wherein the fifth perimeter seam is split to form at least two panels in the liquid circulation area.

40. The apparatus of claim 36 wherein there is no perimeter seam extending into the liquid circulation area from the first perimeter seam, the second perimeter seam, and the third perimeter seam.

41. The apparatus of claim 36 wherein there is no perimeter seam extending into the liquid circulation area from the first perimeter seam, the second perimeter seam, and the third perimeter seam, and the fourth perimeter seam.

42. The apparatus of claim 22 wherein the liquid circulation area may be folded to accommodate various torso sizes.

43. An apparatus for applying a desired temperature to a human body having a torso, at least one leg having a knee, an axillae, and an ilia, with an axillary line defined as running between the axillae, and with an iliac line defined as running between the ilia, the apparatus comprising:
   (a) a leg blanket having an upper leg panel and a lower leg panel separated by an aperture so the leg blanket does not contact the knee;
   (b) a leg blanket having a first perimeter seam, a second perimeter seam, a third perimeter seam and a first liquid circulation area, and the first liquid circulation area is capable of and suitable for encircling a portion of the leg above the knee and a portion of the leg below the knee;
   (c) the leg blanket is shaped to expose the knee; and
   (d) a single first fluid circulation system that allows a first liquid medium to circulate within, the first liquid circulation area in such a manner to effectively transfer the desired thermal property of the first liquid medium to the human body by having the first liquid medium (i) enter the liquid circulation area through a first inlet and (ii) exit the liguid circulation area through a first outlet wherein the first outlet is not the same as the first inlet, and without the first liquid medium contacting the human body.

44. The apparatus of claim 43 further comprising:
   (a) a torso blanket having a sixth perimeter seam, a seventh perimeter seam, an eighth perimeter seam and a second liquid circulation area, and the second liquid circulation area is capable of and suitable for encircling the torso;
   (b) the sixth perimeter seam is shaped to receive the axillae so a portion of the torso blanket extends above the axillary line; and
   (c) a single second fluid circulation system that allows a second liquid medium to circulate within, the second liquid circulation area in such a manner to effectively transfer the desired thermal property of the second liquid medium to the human body by having the second liquid medium (i) enter the second liquid circulation area through a second inlet and (ii) exit the second liguid circulation area through a second outlet wherein the second outlet is not the same as the second inlet, and without the second liquid medium contacting the human body.

45. The apparatus of claim 44 wherein when the seventh perimeter seam is opposite the sixth perimeter seam, the seventh perimeter seam is shaped to receive the ilia so a portion of the torso blanket extends below the iliac line.

46. The apparatus of claim 44 wherein the second liquid medium and the first liquid medium are the same liquid.

47. The apparatus of claim 46 wherein the first liquid medium and the second liquid medium have different temperatures.

48. The apparatus of claim 46 wherein the first liquid medium and the second liquid medium have the same temperature.

49. The apparatus of claim 44 wherein the first liquid medium and the second liquid medium are different liquids.

50. The apparatus of claim 49 wherein the first liquid medium and the second liquid medium have different temperatures.

51. The apparatus of claim 49 wherein the first liquid medium and the second liquid medium have the same temperature.

52. The apparatus of claim 43 further comprising:
   (a) a torso blanket having a ninth perimeter seam, a tenth perimeter seam, an eleventh perimeter seam and a third liquid circulation area, and the third liquid circulation area is capable of and suitable for encircling the torso;
   (b) the ninth perimeter seam is shaped to receive the ilia so a portion of the torso blanket extends above the iliac line; and
   (c) a single second fluid circulation system that allows a third liquid medium to circulate within, the third liquid circulation area in such a manner to effectively transfer the desired thermal property of the third liquid medium to the human body by having the third liquid medium (i) enter the third liquid circulation area through a third inlet and (ii) exit the third liguid circulation area through a third outlet wherein the third outlet is not the same as the third inlet, and without the third liquid medium contacting the human body.

53. The apparatus of claim 52 wherein when the tenth perimeter seam is opposite the ninth perimeter seam, the tenth perimeter seam is shaped to receive the axillae so a portion of the torso blanket extends above the axillary line.

54. The apparatus of claim 52 wherein the second liquid medium and the first liquid medium are the same liquid.

55. The apparatus of claim 54 wherein the first liquid medium and the third liquid medium have different temperatures.

56. The apparatus of claim 54 wherein the first liquid medium and the third liquid medium have the same temperature.

57. The apparatus of claim 52 wherein the first liquid medium and the third liquid medium are different liquids.

58. The apparatus of claim 57 wherein the first liquid medium and the third liquid medium have different temperatures.

59. The apparatus of claim 57 wherein the first liquid medium and the third liquid medium have the same temperature.

* * * * *